(12) United States Patent
Shroff et al.

(10) Patent No.: US 9,578,875 B2
(45) Date of Patent: Feb. 28, 2017

(54) FUNGICIDAL COMPOSITION

(71) Applicant: UPL Limited, Mumbai (IN)

(72) Inventors: Jaidev Rajnikant Shroff, Mumbai (IN); Vikram Rajnikant Shroff, Mumbai (IN); Rajan Ramakant Shirsat, Mumbai (IN)

(73) Assignee: UPL Limited, Mumbai (IN)

( * ) Notice: Subject to any disclaimer, the term of this patent is extended or adjusted under 35 U.S.C. 154(b) by 0 days.

(21) Appl. No.: 14/773,328

(22) PCT Filed: Jan. 29, 2014

(86) PCT No.: PCT/IB2014/058624
§ 371 (c)(1),
(2) Date: Sep. 5, 2015

(87) PCT Pub. No.: WO2014/170764
PCT Pub. Date: Oct. 23, 2014

(65) Prior Publication Data
US 2016/0007593 A1   Jan. 14, 2016

(30) Foreign Application Priority Data
Apr. 16, 2013   (IN) .............................. 416/KOL/2013

(51) Int. Cl.
| | | |
|---|---|---|
| *A01N 25/22* | (2006.01) | |
| *A01N 43/50* | (2006.01) | |
| *A01N 33/04* | (2006.01) | |
| *A01N 47/14* | (2006.01) | |
| *A01N 55/02* | (2006.01) | |

(52) U.S. Cl.
CPC ............. *A01N 25/22* (2013.01); *A01N 43/50* (2013.01); *A01N 47/14* (2013.01); *A01N 55/02* (2013.01)

(58) Field of Classification Search
CPC ......... A01N 25/22; A01N 43/50; A01N 33/04
See application file for complete search history.

(56) References Cited

FOREIGN PATENT DOCUMENTS

| | | |
|---|---|---|
| WO | 9848628 | 11/1998 |
| WO | 2009123346 | 10/2009 |
| WO | 2010021404 | 2/2010 |

*Primary Examiner* — Sahar Javanmard
(74) *Attorney, Agent, or Firm* — Yancy IP Law, PLLC

(57) ABSTRACT

A composition comprising cyazofamid and an organic base, a process for the preparation of such compositions, methods of use thereof and a multi-pack container comprising the composition.

8 Claims, 1 Drawing Sheet

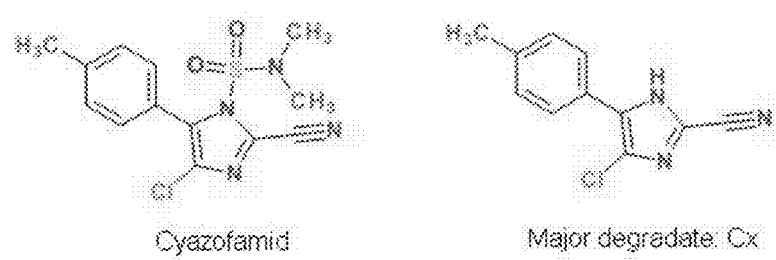
Molecular structure of cyazofamid and major degradate Cx

FUNGICIDAL COMPOSITION

FIELD OF THE INVENTION

The present invention relates to a stable composition of cyazofamid.

BACKGROUND OF THE INVENTION

Cyazofamid (4-chloro-2-cyano-N,N-dimethyl-5-p-tolylimidazole-1-sulfonamide) is an imidazole sulfonamide fungicide introduced by ISHIHARA SANGYO KAISHA, LTD and marketed under the tradename Ranman and having the following chemical structure:

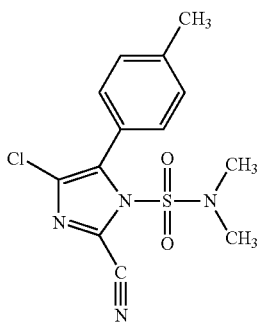 [SMILES: Cc1ccc(-c2c(Cl)nc(C#N)n2S(=O)(=O)N(C)C)cc1]

Cyazofamid has a foliar and soil preventative action with some residual activity. Cyazofamid has very low water solubility and a short hydrolytic half-life.

The article "Photodegradation research of cyazofamid" (Journal of agro environment science, 2009, 28 (1):151-155), disclosed degradative dynamics of 10% cyazofamid suspension on the leaves of cucumber plant and in aqueous solution. It was concluded that cyazofamid had faster degradation rate in the aqueous environment. It was also noted that during the day, the degradative half-life of cyazofamid on leaves of cucumber was 63.6 h, while there was no significant degradation in darkness. Thus, it was concluded that natural light was important factor which affected degradation in natural environment. It was found that the photolytic rate of cyazofamid was accelerated with increasing pH value and temperature and increasing light intensity in aqueous solution, in which the light source and light intensity were the main influencing factor. Therefore, it is recommended that the application of cyazofamid should select low temperature and illumination of weak light in the evening so as to play greater efficacy. There have been numerous other attempts in the art to improve the storage stability of cyazofamid but none too successful.

US 20040039039 discloses synergistic combination of imidazole derivatives (cyazofamid) and a dithiocarbamate (Mancozeb). However, this publication fails to disclose a stable composition of cyazofamid.

WO2009123346 discloses a pesticidal aqueous suspension composition (liquid formulation) comprising a sparingly water-soluble pesticide, an organosilicone surface active agent, a viscosity-reducing agent, an antifoaming agent, a pH adjustor and a dispersant.

WO2010021404 (US2011144175A1) discloses a method for controlling degradation of Cyazofamid in solid formulation by using a stabilizer selected from the group consisting of epoxidized animal oil and/or vegetable oil, a nonionic surface active agent of polyoxyethylene, an anionic surface active agent of polyoxyethylene, a polyhydric alcohol and an inorganic basic substance. The preferred basic substance includes an alkali metal hydroxide, an alkali metal carbonate, an alkali metal bicarbonate, an alkaline earth metal hydroxide, an alkaline earth metal carbonate and an alkaline earth metal bicarbonate.

A need remains in the art for stable formulations of cyazofamid having improved storage stability. The present invention adequately addresses these and other needs existing in the art.

Thus, there is an unfulfilled need in the art for a storage stable formulation comprising cyazofamid with enhanced storage stability and reduced degradation.

SUMMARY OF THE INVENTION

The present invention provides a fungicidal formulation comprising cyazofamid and an organic base.

In another aspect the present invention provides a fungicidal formulation comprising cyazofamid; at least one organic base; and a second pesticidal compound.

In yet another aspect, the present invention provides a fungicidal formulation comprising cyazofamid, at least one organic base; and a second fungicide.

In another aspect, the present invention provides a fungicidal formulation comprising cyazofamid, at least one organic base; and a second fungicide selected from a dithiocarbamate.

In another aspect, the present invention provides a fungicidal formulation comprising cyazofamid, at least one organic base; and mancozeb.

In another aspect, the present invention provides a process for preparation of a fungicidal formulation; said process comprising:
1) admixing cyazofamid and organic base optionally with at least one agrochemically acceptable adjuvant in a blender;
2) milling the admixture of step 1 to obtain a desired particle size;
3) optionally blending the milled material of step 2 to obtain a homogenous mixture;
4) granulating the powder obtained in step 2 ; and
5) drying the granules at a predetermined temperature to a moisture content less than 2%.

In yet another aspect, the present invention provides a process for preparation of fungicidal formulation; said process comprising:
1) admixing cyazofamid; organic base; and a second pesticide optionally with at least one agrochemically effective adjuvant in a blender;
2) milling the admixture of step 1 to obtain a desired particle size;
3) optionally blending the milled material of step 2 to obtain a homogenous mixture;
4) granulating the powder obtained in step 2; and
5) drying the granules at a predetermined temperature to a moisture content less than 2%.

DETAILED DESCRIPTION OF THE PREFERRED EMBODIMENT(S)

The present inventors have found that cyazofamid is inherently unstable as was demonstrated by the 12.5% drop in cyazofamid concentration upon accelerated storage (2 weeks at 54° C.).

BRIEF DESCRIPTION OF ACCOMPANYING FIGURE

FIG. 1: One of the main degradates of cyazofamid which was found to be the hydrolysis product (FIG. 1).

The present inventors observed stability problems with cyazofamid when it was kept in solid form as a technical sample or formulated as a composition. The inventors also found out that use of an inorganic base to stabilize cyazofamid is not successful in inducing storage stability.

It has now been surprisingly found that cyazofamid is unexpectedly storage stable in the presence of an organic base.

Thus, in one aspect, the present invention provides a fungicidal composition comprising cyazofamid and at least one organic base.

The term "fungicidally effective amount" or an "agrochemically effective amount" of cyazofamid or of the second pesticide present within the compositions of the present invention is that quantity of cyazofamid or the second fungicide which when administered in that amount provides a required control of fungi at a locus. The particular amount is dependent upon many factors including, for example, the crop, fungi sought to be controlled and the environmental conditions. The selection of the proper quantity of cyazofamid or the second pesticide to be applied is within the expertise of one skilled in the art and is not considered particularly limiting the scope of the present invention.

In an embodiment, the fungicidally effective amount of cyazofamid comprises about 0.1% to about 90% by total weight of the composition. Accordingly, in this embodiment, the present invention provides a fungicidal composition comprising cyazofamid in an amount of about 3% to about 40% by total weight of the composition and at least one organic base.

In an embodiment, the organic base is present within the compositions of the present invention in a stabilizing effective amount.

The term stabilizing effective amount used in reference to the amount of an organic base in the compositions of the present invention means an amount such that not more than 10% by weight of cyazofamid is degraded upon exposure to 54° C. It may be noted that the stability measurements according to the present invention were directed, in majority, to the stability measurement of cyazofamid owing to the greater susceptibility of cyazofamid to degradation. This should, however, not be construed to mean that the stability of the second pesticide within the compositions of the present invention is not a concern for a person skilled in the art. The present invention achieves an acceptable stability for the second pesticide in addition to the achievement of superior stability for cyazofamid.

In an embodiment, the term "stabilizing effective amount" of an organic base includes references to the presence of an organic base in an amount of about 0.001% to about 18.0% by total weight of the composition.

Accordingly, in an embodiment, the present invention provides a fungicidal composition comprising a fungicidally effective amount of cyazofamid and at least one organic base in an amount of about 0.001% to about 18.0% by total weight of the composition.

In another embodiment, the present invention provides a fungicidal composition comprising cyazofamid in an amount of about 0.1% to about 90% by total weight of the composition and at least one organic base in an amount of about 0.001% to about 18% by total weight of the composition.

In an aspect, the compositions of the present invention comprise a second pesticide. Thus, in this embodiment, the present invention provides a fungicidal composition comprising cyazofamid; at least one organic base; and an agrochemically effective amount of a second pesticide.

The term "agrochemically effective amount" of the second pesticide includes references to an amount of the second pesticide, which is about 0.1% to about 90% by total weight of the composition.

In an embodiment, the second pesticide is any pesticide mentioned in The Pesticide Manual, XVth Edition, BCPC, which is incorporated herein by reference in its entirety.

In an embodiment, the second pesticide is selected from insecticides, fungicides or herbicides.

In another embodiment, the second pesticide is a fungicide. The preferred fungicide may be a pesticide listed as a fungicide in The Pesticide Manual, XVth Edition, BCPC.

In yet another embodiment, the second fungicide is a dithiocarbamate fungicide. The dithiocarbamate fungicide may be selected from mancozeb, maneb, metiram, propineb and zineb.

Thus, in this embodiment, the present invention provides a fungicidal composition comprising cyazofamid; at least one organic base; and a second fungicide selected from the group consisting of mancopper, mancozeb, maneb, metiram, polycarbamate, propineb and zineb.

In a preferred embodiment, the second fungicide is selected from mancozeb, thiophanate-methyl, tribasic copper sulfate, azoxystrobin, chlorothalonil, hexaconazole, a dispersible sulfur composition available as Microthiol DisperSS® or Microthiol® or Microthiol Special Disperss® or a liquid sulphur solution available as Microthiol® Special Liquide.

Therefore, in this embodiment, the present invention provides a fungicidal composition comprising a fungicidally effective amount of cyazofamid; at least one organic base; and a fungicidally effective amount of a fungicide selected from the group consisting of mancozeb, thiophanate-methyl, tribasic copper sulfate, azoxystrobin, chlorothalonil, hexaconazole, a dispersible sulfur composition available as Microthiol DisperSS® or Microthiol® or Microthiol Special Disperss® and a liquid sulphur solution available as Microthiol® Special Liquide.

In another embodiment, the preferred dithiocarbamate fungicide is selected from the group consisting of amobam, asomate, azithiram, carbamorph, cufraneb, cuprobam, disulfiram, ferbam, metam, nabam, tecoram, thiram, urbacide, ziram, dazomet, etem, milneb, mancopper, mancozeb, maneb, metiram, polycarbamate, propineb and zineb, preferably mancozeb.

In another embodiment, the second fungicide is mancozeb. Therefore, in this embodiment, the present invention provides a fungicidal composition comprising cyazofamid; at least one organic base; and mancozeb.

In another embodiment, the present invention provides a fungicidal composition comprising cyazofamid; at least one organic base; and Azoxystrobin.

In another embodiment, the present invention provides a fungicidal composition comprising cyazofamid; at least one organic base; and tribasic copper sulfate.

In another embodiment, the present invention provides a fungicidal composition comprising cyazofamid; at least one organic base; and a dispersible sulfur composition available as Microthiol DisperSS® or Microthiol® or Microthiol Special Disperss®.

In another embodiment, the present invention provides a fungicidal composition comprising cyazofamid; at least one organic base and a liquid sulphur solution available as Microthiol® Special Liquide.

The term "substantial reduction in degradation" herein denotes that such formulation comprising an organic base demonstrates surprisingly reduced degradation of cyazofamid in comparison with the conventional formulation without an organic base According to the present invention, the organic base is preferably an organic amine selected from morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine, Hexamethylenetetramine and tallowamine ethoxylate.

In another embodiment, the organic amine may be selected from the group comprising alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecyclamine, pentadecylamine, hexadecylamine, heptadecylamine, octadecylamine, methylethylamine, methyl isopropylamine, methylhexylamine, methyl nonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, n-hexenyl-2-amine, and propylenediamine; primary aryl amines such as aniline, methoxyaniline, ethoxyaniline, o,m,p-toluidine, phenylenediamine, 2,4,6-tribromoaniline, benzidine, naphthylamine, and o,m,p-chloroaniline; and heterocyclic amines such as pyridine, morpholine, piperidine, pyrrolidine, indoline and azepine.

In another embodiment, it is also possible to use a salt of an organic base, which may be selected from the group consisting of monoalkylammonium, dialkylammonium, trialkylammonium, monoalkenylammonium, dialkenylammonium, trialkenylammonium, monoalkynylammonium, dialkynylammonium, trialkynylammonium, monoalkanolammonium, dialkanolammonium and trialkanolammonium salts.

In yet another embodiment, the preferred organic base is selected from the group consisting of triethanolamine, tallowamine ethoxylate and hexamethylenetetramine.

In another embodiment, the present invention provides a fungicidal composition comprising cyazofamid; at least one organic base selected from triethanolamine, tallowamineethoxylate and hexamethylenetetramine; and a fungicidally effective amount of mancozeb.

In another embodiment, the present invention provides a fungicidal composition comprising cyazofamid; hexamethylenetetramine; and mancozeb.

In another embodiment, the present invention provides a fungicidal composition comprising cyazofamid; hexamethylenetetramine; and Azoxystrobin.

In another embodiment, the present invention provides a fungicidal composition comprising cyazofamid; hexamethylenetetramine; and tribasic copper sulfate.

In another embodiment, the present invention provides a fungicidal composition comprising cyazofamid; hexamethylenetetramine; and a dispersible sulfur composition available as Microthiol DisperSS® or Microthiol® or Microthiol Special Disperss®.

In another embodiment, the present invention provides a fungicidal composition comprising cyazofamid; hexamethylenetetramine and a liquid sulphur solution available as Microthiol® Special Liquide.

In a further preferred embodiment, the preferred organic base is hexamethylenetetramine. Thus, in this embodiment, the present invention provides a fungicidal composition comprising (a) cyazofamid; (b) hexamethylenetetramine; and (c) optionally a second fungicide selected from the group of dithiocarbamates, said group of dithiocarbamates including mancozeb.

In another embodiment, the present invention provides a fungicidal formulation comprising:
 a. cyazofamid;
 b. at least one organic base selected from triethanolamine, hexamethylenetetramine and tallowamineethoxylate; and
 c. one or more agrochemical adjuvants.

In yet another embodiment, the present invention provides a fungicidal composition comprising cyazofamid; at least one organic base selected from triethanolamine, tallowamineethoxylate and hexamethylenetetramine; and mancozeb.

In yet another embodiment, the present invention provides a fungicidal composition comprising cyazofamid, hexamethylenetetramine and mancozeb.

In yet another embodiment, the present invention provides a fungicidal composition comprising cyazofamid, triethanolamine and mancozeb.

In yet another embodiment, the present invention provides a fungicidal composition comprising cyazofamid, tallowamineethoxylate and mancozeb.

In another embodiment, cyazofamid and the organic base are present in the ratio of 5:1 to preferably 5:0.1, either by weight, volume or by molar amount.

In yet another embodiment, cyazofamid and the organic base are present in a ratio of 1:0.2 to 1:0.01 by weight.

In another aspect, the present invention describes a process for the preparation of a fungicidal formulation; said process comprising:
 1) admixing cyazofamid; at least one organic base and surfactants;
 2) milling the admixture of step 1 to obtain a desired particle size;
 3) granulating the powder obtained in step 2 ; and
 4) drying the granules at a predetermined temperature to a moisture content less than 2%.

The granulation techniques of step (3) include fluidized-bed granulation, spray drying, pan agglomeration and extrusion.

In an embodiment, cyazofamid and the organic base are admixed in the presence of at least one agrochemically acceptable excipient.

In a preferred embodiment, cyazofamid and the organic base are blended in the presence of at least one agrochemically acceptable excipient.

In another embodiment, the milling of the blend obtain in step (a) is performed in an air jet mill, although other milling devices are not specifically excluded.

In another embodiment, the milled material is blended to obtain a homogenous mixture prior to being mixed with the second mixture for extrusion.

In yet another embodiment, the extruded granules are preferably dried at a pre-determined temperature of 70-75° C. although the selection of the precise temperature is not limiting.

In an embodiment, the fungicidal composition of the present invention comprises cyazofamid and mancozeb in a predetermined ratio of about 1:16.

In yet another aspect, the present invention provides a process for the preparation of a fungicidal formulation; said process comprising;
1) admixing cyazofamid and at least one organic base optionally with other adjuvants and mancozeb in a blender;
2) milling the blend of step 1 through air jet mill to get a desired particle size;
3) blending the milled material of step 2 to obtain a homogenous mixture;
4) Granulating the powder obtained in step 3; and
5) drying the granules at temperature of about 70-75° C. having moisture content less than 2%.

The fungicidal combination of the present invention is preferably formulated as a solid composition including, but not limited to, dust, powder, granules, pellets, tablets, dry flowable, wettable powder or water dispersible granules.

In an embodiment, the formulation of the present invention further comprises an agrochemically acceptable carrier. These carriers may be organic or inorganic material which may be combined with the active ingredients so as to facilitate better spreadability as well as enable better contact with the target fungi. These carriers must be agriculturally acceptable and environmentally friendly. Carriers may include such dispersing agents, antifoaming agents, pH modifiers, surfactants, and other fillers which may be added into a stable composition.

In an embodiment, the composition of each or any aspect or embodiment described hereinabove comprises at least one adjuvant selected from at least one wetting agent, at least one antifoam, at least one pH modifier, at least one surfactant and combinations thereof. The composition content of these adjuvants is not particularly limiting and may be determined by a skilled technician in the art according to the conventional protocols.

In one embodiment, the composition may contain ionic and nonionic dispersing agents to enable disintegration of granules in water with ease, such as salts of polystyrenesulphonic acids, salts of polyvinylsulphonic acids, salts of naphthalenesulphonic acid/formaldehyde condensates, salts of condensates of naphthalenesulphonic acid, phenolsulphonic acid and formaldehyde, and salts of lignosulphonic acid, polyethylene oxide/polypropylene oxide block copolymers, polyethylene glycol ethers of linear alcohols, reaction products of fatty acids with ethylene oxide and/or propylene oxide, furthermore polyvinyl alcohol, polyvinylpyrrolidone, copolymers of polyvinyl alcohol and polyvinylpyrrolidone and copolymers of (meth)acrylic acid and (meth)acrylic esters, furthermore alkyl ethoxylates and alkylaryl ethoxylates. The preferred dispersing agents include sodium naphthalene sulfonate-formaldehyde condensate, alkyl naphthalene sulfonate or a combination thereof.

In an embodiment, the compositions of the present invention comprise at least one wetting agent selected from soaps; salts of aliphatic monoesters of sulphuric acid including but not limited to sodium lauryl sulphate; sulfoalkylamides and salts thereof including but not limited to N-methyl-N-oleoyl-taurate Na salt; alkylarylsulfonates including but not limited to alkylbenzenesulfonates; alkylnaphthalenesulfonates and salts thereof and salts of ligninsulfonic acid. In an embodiment, the wetting agent includes a blend comprising an alkali metal salt of alkylnaphthalenesulfonate or an alkali metal salt of ligninsulfonic acid or a combination thereof.

In a preferred embodiment, the composition of the present invention comprises a wetting component comprising a wetting agent selected from an alkali metal salt of alkylnaphthalenesulfonate or an alkali metal salt of ligninsulfonic acid or a combination thereof.

In an embodiment, the compositions of the present invention comprise at least one antifoaming agent which is usually employed for this purpose in agrochemical compositions. In an embodiment, the preferred antifoaming agents are selected from silicone oil and magnesium stearate or a suitable combination thereof.

In an embodiment, the compositions of the present invention comprise at least one further surfactant selected from salts of polystyrenesulphonic acids; salts of polyvinylsulphonic acids; salts of naphthalenesulphonic acid/formaldehyde condensates; salts of condensates of naphthalenesulphonic acid, phenolsulphonic acid and formaldehyde; salts of lignosulphonic acid; polyethylene oxide/polypropylene oxide block copolymers; polyethylene glycol ethers of linear alcohols; reaction products of fatty acids with ethylene oxide and/or propylene oxide; polyvinyl alcohol; polyvinylpyrrolidone; copolymers of polyvinyl alcohol and polyvinylpyrrolidone; copolymers of (meth)acrylic acid and (meth)acrylic esters; and alkyl ethoxylates and alkylarylethoxylates.

In another aspect, the present invention provides a method of treating a fungal infestation at a locus by treating said locus with a composition comprising cyazofamid and an organic base.

In an embodiment, the method comprises treating a fungal infestation at a locus by treating the locus with a composition comprising cyazofamid, an organic base and a second fungicide.

The term locus as used herein shall denote the vicinity of a desired crop in which fungal control is desired.

The locus includes the vicinity of desired crop plants wherein the fungal infestation has occurred or is expected to occur. The term crop shall include a multitude of desired crop plants or an individual crop plant growing at a locus.

The term control indicates eradication of the investigated fungii. A 100% control signifies total eradication of the fungi under investigation.

In another aspect, the present invention provides a method of treating a fungal infestation at a locus by treating said locus with a composition comprising cyazofamid, hexamethylenetetramine and mancozeb.

In an embodiment, the composition comprising cyazofamid and optionally Mancozeb are particularly useful against treating Late blight (*Phytophthora infestans*), early and late blight (*Phytophthora infestans, Alternaria solani*), downy mildew (*Plasmopara viticola, Pseudo-peronospora-* cubensis and *Peronospora tabacina*) on crops such as Potato, tomato, Grapes, Cucumber, watermelon and pepper.

In another aspect, the present invention provides a method of treating a fungal infestation at a locus by treating said locus with a composition comprising cyazofamid, hexamethylenetetramine and Azoxystrobin.

In another aspect, the present invention provides a method of treating a fungal infestation at a locus by treating said locus with a composition comprising cyazofamid, hexamethylenetetramine and tribasic copper sulfate.

In another aspect, the present invention provides a method of treating a fungal infestation at a locus by treating said locus with a composition comprising cyazofamid, hexamethylenetetramine and a dispersible sulfur composition available as Microthiol DisperSS® or Microthiol® or Microthiol Special Disperss®.

In another aspect, the present invention provides a method of treating a fungal infestation at a locus by treating said locus with a composition comprising cyazofamid, hexamethylenetetramine and a liquid sulphur solution available as Microthiol® Special Liquide.

In another aspect, the compositions of the present invention may be presented in the form of a multi-pack fungicidal product or as a kit-of-parts for fungicidal treatment of plants.

In an embodiment of the multi-pack fungicidal product, the organic base may be contained in a separate container or it may be contained in the same container as cyazofamid. Preferably, when the organic base is contained in a separate container, the multi-pack fungicidal product includes an instruction manual instructing an user to admix the organic base into the container containing cyazofamid immediately upon its opening to the external environment.

Therefore, in one embodiment, the present invention provides a multi-pack fungicidal product, comprising:
 (a) a first container comprising cyazofamid;
 (b) a second container comprising one of the compounds selected from mancozeb, azoxystrobin, tribasic copper sulfate, Microthiol DisperSS® or Microthiol® or Microthiol Special Disperss® or Microthiol® Special Liquide, thiophanate-methyl, chlorothalonil and hexaconazole;
 (c) a third container containing an organic base selected from hexamethylenetetramine, triethanolamine and tallowamineethoxylate; and
 (d) an instruction manual instructing an user to admix the organic base contained in the third container into the first container containing cyazofamid immediately upon its being opened.

In yet another embodiment, the present invention provides a multi-pack fungicidal product, comprising:
 (a) a first container comprising cyazofamid;
 (b) a second container comprising mancozeb;
 (c) a third container containing hexamethylenetetramine; and
 (d) an instruction manual instructing an user to admix hexamethylenetetramine contained in the third container into the first container containing cyazofamid immediately upon its being opened.

In an embodiment, the multi-pack fungicidal product comprises a package holding the first, second and third containers together with the instruction manual.

In this embodiment, the present invention provides a multi-pack fungicidal product, comprising:
 (a) a first container comprising cyazofamid and an organic base selected from hexamethylenetetramine, triethanolamine and tallowamineethoxylate;
 (b) a second container comprising one of the compounds selected from mancozeb, azoxystrobin, tribasic copper sulfate, Microthiol DisperSS® or Microthiol® or Microthiol Special Disperss® or Microthiol® Special Liquide, thiophanate-methyl, chlorothalonil and hexaconazole; and
 (c) a package holding the first and second containers.

In yet another embodiment, the present invention provides a multi-pack fungicidal product, comprising:
 (a) a first container comprising cyazofamid and hexamethylenetetramine;
 (b) a second container comprising mancozeb; and
 (c) a package holding the first and second containers.

The formulation described above is fungicidally efficacious and stable. The granules obtained by the process have superior attrition resistance, disperse rapidly in water and have good suspensibility in water once dispersed.

EXAMPLES

The following examples illustrate embodiments of the proposed invention that are presently best known. However, other embodiments can be practiced that are also within the scope of the present invention. All of the agrochemical formulations, according to the scope of the present invention and exemplified below had excellent storage stability properties.

Example 1:

| Sr. No. | Ingredient | Quantity (g) |
|---------|-----------|--------------|
| 1 | Mancozeb Technical purity 85.5% | 82.69 |
| 2 | Cyazofamid Technical purity 95% | 5.89 |
| 3 | Sodium lignosulfonate | 8.02 |
| 4 | Hexamethylenetetramine | 0.99 |
| 5 | Alkyl Naphthalene Sulfonate Sodium Salt | 2.5 |
| | Total | 100 |

Process of Manufacturing:

The required quantities of Mancozeb and cyazofamid along with Hexamethylenetetramine and Sodium lignosulfonate were blended in a ribbon blender and milled in an air jet mill. The milled mixture was again blended in ribbon blender to obtain a homogenous mixture. A second mixture of a defoamer and water was added to the homogenous mixture to prepare a dough. The dough was extruded to get granules. The extruded granules were dried to obtain granules with moisture content less than 2%.

Example 2:

| Sr No | Ingredient | Quantity (g) |
|-------|-----------|--------------|
| 1 | Cyazofamid Technical purity 95% | 94.74 |
| 2 | Alkyl Naphthalene Sulfonate Sodium Salt | 1 |

-continued

| Sr No | Ingredient | Quantity (g) |
|---|---|---|
| 3 | Sodium lignosulfonate | 3.27 |
| 4 | Hexamethylenetetramine | 0.99 |
|   | Total | 100 |

Experiment: Cyazofamid technical was mixed with $Na_2CO_3$ (Inorganic base) in one batch and with HMT (organic base) in the other. Both the samples were kept at 54° C. for 14 days. After 14 days, the cyazofamid content in both the samples was analyzed. Cyzofamid technical demonstrated unexpectedly improved stability in organic base compared to Inorganic base even in absence of above adjuvants.

|       |            | Stability after storage at 54° C. |        |        |        |
|-------|------------|------------|------------|------------|------------|
|       |            | Na2CO3 0.5% |            | HMT 0.5% |            |
| Sr. No | Parameters | 0 Day | 14 Day | 0 Day | 14 Day |
| 1 | Cyazofamid Technical | 95.98 | 92.38 | 95.10 | 94.27 |
| 2 | % Degradation |  | 3.75 |  | 0.87 |

Process of Manufacturing:

The required quantities of cyazofamid along with Hexamethylenetetramine and Sodium lignosulfonate were blended in a ribbon blender and milled in an air jet mill. The milled mixture was again blended in ribbon blender to obtain a homogenous mixture. A second mixture of a defoamer, and a wetting agent (alkyl naphthalene sulfonate sodium salt) and water was added to the homogenous mixture to prepare dough. The dough was extruded to get granules. The extruded granules were dried to obtain granules with moisture content less than 2%.

Example 3:

The following compositions comprising cyazofamid and Mancozeb were prepared, with the different stabilizers substituted. The AHS stability of these formulations was tested.

| Sr No | Batch No | Cyazofamid content 14 d Ambient | Cyazofamid content after 14 D AHS at 54° C. | Degradation in Cyazofamid content after 14 D AHS at 54° C. |
|---|---|---|---|---|
| 3(a) | Mancozeb + Cyazofamid + 0.8% Triethanol Amine | 6.34 (% w/w) | 5.90 | 6.94% |
| 3(b) | Mancozeb + Cyazofamid + 1% Tallow Amine Ethoxylate 15 EO | 6.11 (% w/w) | 5.59 | 8.51% |
| 3(c) | Mancozeb Technical (82.89%) + Cyazofamid Technical (5.91%) and HMT (0.9%). | 5.73 | 5.51 | 3.83% |
| 3(e) | Suspensibility of example 3(c) | 76.4 | 67.55 | — |
| 3(f) | Suspensibility of example 3(b) | 70.69 | 67.45 | — |
| 3(e) | Suspensibility of example 3(a) | 78.24 | 75.69 | — |

From the above it is evident that there is reduction in the degradation of cyazofamid in the presence of organic amine base.

Comparative Examples

Example 4

The stability of cyazofamid technical was tested in the presence of an inorganic base and compared with the stability in the presence of an organic base, with the following results:

|       |            | Presence of 0.5% $Na_2CO_3$ |        |        | Presence of 0.5% HMT |        |        |
|---|---|---|---|---|---|---|---|
| Sr. No. | Parameters | 0 D | 14 D AHS at 54° C. | Degradation (%) | 0 D | 14 D AHS at 54° C. | Degradation (%) |
| 1 | Cyazofamid content (%, w/w) | 95.98 | 92.38 | 3.75 | 95.1 | 94.27 | 0.87 |

Example 5

The formulation prepared according to Example 1 (adjusted for purity of the technical material) was modified to replace the HMT content with 1.0% sodium carbonate. The stability of both the formulations were tested, with the following results:

|       |            | Presence of 1.0% $Na_2CO_3$ |        |        | Presence of 1.0% HMT |        |        |
|---|---|---|---|---|---|---|---|
| S No. | Parameters | 0 D | 14 D AHS at 54° C. | Degradation (%) | 0 D | 14 D AHS at 54° C. | Degradation (%) |
| 1 | Mancozeb content (%, w/w) | 70.67 | 70.49 | 0.25 | 70.34 | 70.14 | 0.28 |
| 2 | Cyazofamid content (%, w/w) | 6.27 | 5.57 | 11.16 | 5.59 | 5.43 | 2.86 |

Reference Example 6

The present inventors conducted stability studies with cyazofamid technical material as such and in the presence of 1% acid, 1% alkali and 1% water. It was found that all four samples degraded heavily even when the four tested samples were stored in tight glass bottles with plug and cap. All the four samples were found to be heavily degraded under AHS conditions, which confirmed the instability of cyazofamid.

In Expt. 6A, Cyazofamid technical (as such) was filled in 3 glass bottles with air tight plug and cap. One bottle was kept in refrigerator maintained at 10°±1° C., second bottle was stored at room temperature and the third bottle was stored in an incubator maintained at 54°±2° C.

In Expt 6B, Cyazofamid technical was mixed with 1% Acid (Acid used was 10% HCl) in a mixer grinder. This mixture was filled in 3 glass bottles with air tight plug and cap. One bottle was kept in refrigerator maintained at 10°±1° C., second bottle was stored at room temperature and the third bottle was stored in an incubator maintained at 54°±2° C.

In Expt 6C, Cyazofamid technical was mixed with 1% Alkali (Alkali used was 10% NaOH) in a mixer grinder. This mixture was filled in 3 glass bottles with air tight plug and cap. One bottle was kept in refrigerator maintained at 10°±1° C., second bottle was stored at room temperature and the third bottle was stored in an incubator maintained at 54°±2° C.

In Expt 6D, Cyazofamid technical was mixed with 1% water in a mixer grinder. This mixture was filled in 3 glass bottles with air tight plug and cap. One bottle was kept in refrigerator maintained at 10°±1° C., second bottle was stored at room temperature and the third bottle was stored in an incubator maintained at 54°±2° C.

All the samples were stored at the respective conditions for 14 days. After 14 days, Cyazofamid content in all the samples was measured under identical conditions, and the results were compiled.

Advantages of one or more embodiments of the present invention:
1. The formulations according to the present invention possess enhanced stability.
2. There is substantial reduction in the degradation of cyazofamid due to presence of an organic base.
3. The formulation of cyazofamid and mancozeb is found to be stable with substantial reduction in the degradation of cyazofamid.
4. The formulations according to the present invention show superior suspension stability.
5. The formulations prepared according to present invention have superior attrition resistance, disperse rapidly in water and have good suspensibility in water once dispersed.

The invention has been described above with reference to the specific examples. It should be noted that the examples appended above illustrate rather than limit the invention and that those skilled in the art will be able to design many alternate embodiments without departing from the spirit of the invention. Other than in the operating examples provided hereinbefore or where otherwise indicated, all numbers expressing quantities of ingredients are to be understood as being modified in all instances by the term about.

The invention claimed is:

1. A fungicidal composition comprising cyazofamid and an organic base selected from the group consisting of Hexamethylene tetramine.

2. The composition as claimed in claim 1 comprising cyazofamid in an amount of 0.1% to 90% by weight of the composition.

3. The composition as claimed in claim 1 comprising the organic base in an amount of 0.001% to 18% by weight of the composition.

4. The composition as claimed in claim 1 comprising a second pesticide.

5. The composition as claimed in claim 1 wherein the second pesticide is mancozeb.

6. The composition as claimed in claim 1, wherein the second pesticide is a fungicide selected from mancozeb, thiophanate-methyl, tribasic copper sulfate, azoxystrobin, chlorothalonil, hexaconazole, a dispersible sulfur composition or a liquid sulphur solution.

| Sr No | Sample | Purity after 14 days of storage at 10° C. | Room temperature (30-35° C.) | Purity after 14 days of storage at 54 ± 2° C. | Degradation with respect to storage at ambient condition |
|---|---|---|---|---|---|
| 1 | Cyazofamid Technical (As Such) | 95.36 | 95.55 | 83.25 | 12.87% |
| 2 | Cyazofamid Technical + 1% Acid (Acid used was 10% HCl) | 95.38 | 92.96 | 76.05 | 18.19% |
| 3 | Cyazofamid Technical + 1% Alkali (Alkali used was 10% NaOH) | 95.31 | 94.53 | 69.95 | 26.00% |
| 4 | Cyazofamid Technical + 1% Water | 95.24 | 95.02 | 70.26 | 26.05% |
| 5 | Cyazofamid technical (99%) + 1% HMT | 99.0 | 95.10 | 94.27 | 0.87 |

7. The composition as claimed in claim 1 comprising one or more agrochemically acceptable adjuvants.

8. The composition as claimed in claim 7, wherein the adjuvant is selected from at least one wetting agent, at least one antifoam, at least one pH modifier, at least one surfactant and combinations thereof.

* * * * *